United States Patent [19]

Clement et al.

[11] Patent Number: 5,198,513

[45] Date of Patent: Mar. 30, 1993

[54] REACTIVE COMPOUNDS CONTAINING PERFLUOROVINYL GROUPS

[75] Inventors: Katherine S. Clement; David A. Babb; Bobby R. Ezzell; W. Frank Richey, all of Lake Jackson, Tex.

[73] Assignee: The Dow Chemical Company, Midland, Mich.

[21] Appl. No.: 668,294

[22] Filed: Mar. 12, 1991

Related U.S. Application Data

[62] Division of Ser. No. 364,666, Jun. 9, 1989, Pat. No. 5,037,919.

[51] Int. Cl.$^5$ .................. C08F 12/20; C08F 12/30; C08F 12/22; C08F 259/08
[52] U.S. Cl. .................. 526/242; 526/243; 526/244; 526/245; 526/246; 526/247; 526/248; 525/276
[58] Field of Search ............... 525/276; 526/242, 243, 526/244, 245, 246, 247, 248, 249

[56] References Cited

U.S. PATENT DOCUMENTS

| Re. 34. 32,1 | 7/1986 | Carlson | 526/247 |
|---|---|---|---|
| 2,404,374 | 7/1946 | Harmon | 570/132 |
| 2,671,799 | 8/1950 | Miller | 558/337 |
| 2,848,504 | 8/1958 | Dixon | 570/132 |
| 2,922,823 | 1/1960 | Tarrant | 570/132 |
| 2,958,685 | 11/1960 | Eleuterio | 526/192 |
| 2,982,786 | 2/1961 | McCane | 568/669 |
| 3,022,356 | 2/1962 | Nooy | 568/842 |
| 3,111,509 | 11/1963 | Folt | 526/249 |
| 3,114,778 | 12/1963 | Fritz et al. | 568/674 |
| 3,277,068 | 10/1966 | Wall et al. | 522/181 |
| 3,303,145 | 2/1967 | Carlson | 528/402 |
| 3,310,606 | 3/1967 | Fritz | 525/276 |
| 3,316,312 | 4/1967 | McCane et al. | 570/132 |
| 3,505,411 | 4/1970 | Rice | 568/615 |
| 3,546,186 | 12/1970 | Gladding et al. | 526/247 |
| 3,549,606 | 12/1970 | Gash | 526/247 |
| 3,682,876 | 6/1972 | Anderson et al. | 522/66 |
| 3,696,154 | 10/1972 | Anderson | 568/45 |
| 3,840,603 | 10/1974 | Anderson et al. | 526/247 |
| 3,900,380 | 8/1975 | Anderson et al. | 522/5 |
| 3,926,989 | 12/1976 | Rebsdat et al. | 544/174 |
| 4,154,753 | 5/1979 | Fielding | 558/201 |
| 4,166,165 | 8/1979 | Hisasue et al. | 526/247 |
| 4,281,092 | 7/1981 | Breazeale | 526/247 |
| 4,326,046 | 4/1982 | Miyaka et al. | 525/276 |
| 4,330,654 | 5/1982 | Ezzel et al. | 526/243 |
| 4,341,685 | 7/1982 | Miyaka et al. | 526/245 |
| 4,377,711 | 3/1983 | Rico et al. | 568/588 |
| 4,423,249 | 12/1983 | Carl et al. | 568/655 |
| 4,474,899 | 10/1984 | Resnick | 526/245 |
| 4,530,972 | 7/1985 | Tatemoto et al. | 526/249 |
| 4,564,717 | 1/1986 | Ohmori et al. | 526/249 |
| 4,975,502 | 12/1990 | Morita et al. | 526/247 |
| 5,001,278 | 3/1991 | Oka et al. | 526/242 |

FOREIGN PATENT DOCUMENTS

| 0296559 | 12/1988 | European Pat. Off. | 526/247 |
|---|---|---|---|
| 303292 | 2/1989 | European Pat. Off. | |
| 0330240 | 6/1989 | European Pat. Off. | 526/247 |
| 2822116 | 11/1978 | Fed. Rep. of Germany | 526/247 |
| 3024018 | 1/1981 | Fed. Rep. of Germany | |
| 1481730 | 4/1967 | France | |
| 55-29519 | 3/1980 | Japan | 526/245 |
| 1218610 | 9/1986 | Japan | 526/249 |
| 1126554 | 9/1968 | United Kingdom | |
| 1185564 | 3/1970 | United Kingdom | |
| 8602072 | 4/1986 | World Int. Prop. O. | |
| 9015042 | 12/1990 | World Int. Prop. O. | |
| 9015043 | 12/1990 | World Int. Prop. O. | |
| 9015044 | 12/1990 | World Int. Prop. O. | |
| 9015082 | 12/1990 | World Int. Prop. O. | |

OTHER PUBLICATIONS

U.S. Application Ser. No. 364,667 filed Jun. 9, 1989.
U.S. Application Ser. No. 534,819 filed Jun. 7, 1990.
U.S. Application Ser. No. 364,666 filed Jun. 9, 1989.
U.S. Application Ser. No. 364,686 filed Jun. 9, 1989.
U.S. Application Ser. No. 364,665 filed Jun. 9, 1989.
U.S. Application Ser. No. 451,404 filed Dec. 15, 1989.
U.S. Application Ser. No. 668,296 filed Mar. 12, 1991.
U.S. Application Ser. No. 668,295 filed Mar. 12, 1991.
U.S. Application Ser. No. 673,882 filed Mar. 22, 1991.
U.S. Application Ser. No. 673,884 filed Mar. 22, 1991.
U.S. Application Ser. No. 625,588 filed Dec. 10, 1990.
Chemical Abstract 59:8879c.
Chemical Abstract 77:34091k.
Chemical Abstract 105:171569h.
Chemical Abstract 110:181626.

(List continued on next page.)

*Primary Examiner*—Paul R. Michl
*Assistant Examiner*—Peter Szekely

[57] ABSTRACT

A compound having at least one perfluorovinyl group and at least one functional group is suitable for reacting with and/or forming polymers. The compound is preferably of Formula I:

$$(G)_n\text{-}R\text{-}(X\text{---}CF\text{=}CF_2)_m$$

wherein R represents an optionally substituted hydrocarbyl group, X represents any group which links R and a perfluorovinyl group; n is the number of G groups, m is the number of (XCF=CF$_2$) groups; and G represents any reactive functional group or a group convertible into a reactive functional groups.

A process for preparing a compound of Formula I comprises the steps of:

(a) preparing a 2-halotetrafluoro compound of the Formula III:

$$(Q\text{---}CF_2\text{---}CF_2\text{-}X)_m\text{-}R\text{-}(G'')_n$$

wherein R, X, m and n are as described for Formula I and Q is bromine, chlorine or iodine; and G" is a functional group, or a functional group suitable for conversion into G;

(b) chemically modifying group G" to produce functional group G; and (c) dehalogenating the 2-halotetrafluoro compound to form the corresponding trifluorovinyl compound.

29 Claims, No Drawings

OTHER PUBLICATIONS

Coffman, Barrick, Cramer and Raasch in *J. Amer. Chem. Soc. vol. 71* (1949) pp. 490–496, "Synthesis of Tetrafluoro Cyclobutanes by Cycloalkylation".

Henne and Ruh in J. Amer. Chem. Soc. 69, 279–281 (1947).

Maurice Prober in J. Amer. Chem. Soc. 75, 968–973 (1953).

Hauptschein et al in J. Amer. Chem. Soc. 79, 2549–2553 (1957).

Miller et al. in J. Amer. Chem. Soc. 83, 1767–1768 (1961).

Brown et al. in J. Poly. Sci. Part A-1, vol. 3, (1965) pp. 1641–1660.

Brown et al. in *J. Poly Sci. Part A-1, vol. 34 (1966) pp. 131–1140.*

Banks, et al. in J. Chem. Soc. (C), 22 (1966) pp. 2051–2052.

Sharkey in Fluorine Chem. Rev. 2, 1–53 (1968).

Crawford in J. Chem. Soc. (C), 1967 pp. 2395–2396.

Hodgdon and Macdonald in J. Poly Sci. Part A-1, vol. 6, (1968) pp. 711–717.

Chambers in Fluorine in Organic Chemistry, John Wiley, New York, (1973) pp. 173–191 and 199–208.

Rico and Waselman in *J. Fluorine Chemistry*, 20 (1982) pp. 759–764.

Heinze and Burton in J. Org. Chem. 1988, 53, pp. 2714–2720.

Paleta et al., "Haloacrylic acids VI, Ethylene glycol bis(trifluoroacrylate)" Sb. Vsy. Sk. Chem.-Technol. 1976, (C23, 5–11 (1976).

A. A. Glazkov et al., "Cycloaddition of Perfluorovinyl Ethers to Dienes," Bulletin of the Academy of Sciences of the USSR.

P. Tarrant et al., The Preparation and Reactions of some Silanes containing the Trifluorovinyl group, J. Org. Chem. vol. 31, No. 4, Apr. 1966, pp. 1143–1146.

Drysdale, Gilbert, Sinclair and Sharkey J. Amer. Chem. Soc. vol. 80 (1958) pp. 3672–3675.

McBee, Hsu, Pierce and Roberts in "Diels–Alder Reactions with Fluorine-Containing Olefins" in *J. Amer. Chem. Soc. vol. 77 (1955) pp. 915–917.*

Chambon and Winter in J. of Rheology 31 (1987) pp. 683–697.

Perry in Fluotine Chemistry Reviews 1 (2) (1967) pp. 253–313.

Nijenhuis and Winter in Macromolecules 22 (1989) pp. 411–414.

Winter and Chambon in J. of Rheology, 30 (2) (1986) pp. 367–382.

REACTIVE COMPOUNDS CONTAINING PERFLUOROVINYL GROUPS

CROSS-REFERENCE TO RELATED APPLICATION

This is a divisional of application Ser. No. 07/364,666, filed Jun. 9, 1989 now U.S. Pat. No. 5,037,919.

This invention relates to compounds having at least one perfluorovinyl group and at least one other functional group and to polymeric compositions prepared from such compounds.

High molecular weight enhances the physical properties of engineering thermoplastics such as polycarbonates, polyesters, polyamides, and polyethers. However, high molecular weight also increases melt viscosity which often causes difficulty in processing these polymers into useful articles. One way to overcome the difficulty is to build lower molecular weight polymers which are easily fabricated, then to increase chain length after or during fabrication by a continuation of the condensation reaction on which polymer formation is based. However, these condensation reactions almost always produce small molecule by-products such as water, hydrogen chloride, or salts which are difficult to remove from a finished article and which are almost always detrimental to the properties of the final product.

This undesirable situation can be overcome by capping lower molecular weight polymers (oligomers) with molecules (capping agents) which contain terminal functional groups which will react with each other when the molded article is heated above a given temperature or during the molding operation itself. However, almost all capping agents have terminal functionality such as ethenyl or ethynyl groups which under high temperature conditions create a cross-linked, thermoset polymer system. This often produces a brittle material which forfeits many of the desirable qualities of thermoplastic polymers.

Acetylene terminated systems (ATS) illustrate such capping and are reported by Hergenrother et al. in *SAMPE Journal* Sep./Oct. 1984 pp. 18-23; *ChemTech*, 1984, pp. 496-502; and *Polymer Preprints, Amer. Chem. Soc.* 1983, Vol. 24, no. 2, pp. 16-17; and *J. Macromolecular Sci, Reviews in Macromolecular Chemistry* C19(1), 1, (1980). These materials are frequently brittle due to high crosslink densities and must be carefully purified to avoid lowered thermooxidative stability. (Abrams et al., in *Organic Coatings and Applied Polymer Science Proceedings*, Vol. 48, pp. 909-913 (1983).)

It would be very desirable to have a capping agent to react with oligomers such that these oligomers would have a terminal functionality which, when heated, would extend the polymer chain linearly, without crosslinking, and without the consequent formation of volatiles or salts.

SUMMARY OF THE INVENTION

In one aspect, the invention is a compound of Formula I:

$$G_n\text{-R-}(X\text{—}CF\text{=}CF_2)_m$$

wherein R represents an optionally substituted hydrocarbyl group, X represents any group which links R and a perfluorovinyl group; n is the number of G groups, m is the number of $-(X-CF=CF_2)$ groups, and G represents any reactive functional group or any group convertible into a reactive functional group.

In another aspect, the invention is a process for preparing compounds of Formula I comprising the steps of:

(a) preparing a 2-halotetrafluoro compound of the Formula III:

$$(Q\text{—}CF_2\text{—}CF_2\text{-X-})_m\text{-R-}(G'')_n$$

wherein X, R, m and n are as defined for Formula I, and Q is bromine, chlorine or iodine; and G" is a functional group G, as previously defined, or a functional group suitable for conversion into G;

(b) chemically modifying group G" to produce functional group G; and (c) dehalogenating the 2-halotetrafluoro compound to form the corresponding trifluorovinyl compound.

In yet another aspect, the invention is the reaction product of a compound of Formula I with a second compound having at least one functional group reactive with the reactive functional group G of the first compound.

Compounds of the invention are particularly useful in reacting with such second compounds as oligomers, di- or poly-functional compounds and relatively low molecular weight polymers to produce materials having a perfluorovinyl group. Advantageously, such materials with perfluorovinyl groups are cyclodimerized to increase the molecular weight of the materials. Cyclodimerization is a particularly useful means of increasing molecular weight because it links molecules, particularly oligomers and polymers linearly rather than crosslinking them and does so without production of volatile by-products which can cause undesirable bubbles in polymeric materials.

DETAILED DESCRIPTION OF THE INVENTION

The invention includes compounds having at least one perfluorovinyl group and at least one functional group suitable for forming condensation polymers or a group suitable for conversion into such a functional group. The functional group is preferably attached indirectly to the perfluorovinyl group via some linking structure thereto. More preferably, the compounds have structures represented by Formula I:

$$G_n\text{-R-}(X\text{—}CF\text{=}CF_2)_m$$

wherein R represents an optionally substituted hydrocarbyl group, X represents any group which links R and a perfluorovinyl group; n is the number of G groups, preferably an integer of from 1 to about 4, more preferably from 1 to about 2; m is the number of $(-X-CF=CF_2)$ groups, preferably an integer of from 1 to about 3, more preferably from about 1 to about 2; G represents any reactive functional group or any group convertible into a reactive functional group, preferably any functional group suitable for reaction with di- or polyfunctional compounds to form polymers, which functional group (G) is, more preferably, insufficiently nucleophilic to react undesirably with perfluorovinyl groups at room temperature (e.g. 25° C.), most preferably at temperatures used in subsequent reactions of the compound. Alternatively, G is a group suitable for chemical conversion into a functional group suitable for reaction to form a polymer.

G is preferably selected from the group consisting of functional groups including hydroxyl groups (both alcoholic and phenolic), carboxylic acid groups, acyl halides such as chlorides, isocyanates, acyl azides, acetyl groups, primary or secondary amines, sulfide groups, sulfonic acid groups, sulfonamide groups, ketones, aldehydes, epoxy groups, primary or secondary amides, halo groups (e.g. chloro, bromo, iodo, and fluoro groups), nitro groups, cyano groups, anhydrides, imides, cyanate groups, vinyl, allyl, acetylene groups; and esters including thiocarboxylic and carboxylic esters, preferably lower alkyl esters such as methyl and ethyl esters, trihalomethyl groups including trichloromethyl groups, silicon-containing substituents such as alkyl silanes, siloxanes, chlorosilanes, phosphorus-containing groups such as phosphines, phosphate, phosphonate, boron-containing groups such as boranes, alkyl groups and alkoxy groups preferably containing from about 1 to about 12 carbon atoms when R is aromatic and the like. Most preferably, for ease in preparation of the compounds and polymers thereof, G is selected from hydroxyl, carboxylic or thiocarboxylic acid ester groups, carboxylic acid groups, acyl chlorides, isocyanates, alkyl groups when R is aromatic, and primary or secondary amines.

X is any linking group such as an oxygen atom, carboxylic and thiocarboxylic ester groups, other sulfur containing structures, perfluoroalkylene, perfluoroalkylene ether, alkylene, acetylene, phosphorus containing groups such as phosphines, carbonyl and thio carbonyl groups; seleno: telluro: nitrido; silicon-containing groups such as silanediyl, trisilanediyl tetrasilanetetrayl, siloxanediyl, disiloxanediyl, trisiloxyl, trisilazanyl, or silylthio groups; boron-containing groups such as boranediyl or methylboranediyl groups; a combination thereof, or any other group which is inert, which molecularly links R to a perfluorovinyl group, and which provides a molecular structure in which the perfluorovinyl group is sufficiently reactive to form a perfluorocyclobutane ring. For instance, X is preferably other than a perfluoroalkylene group because perfluorovinyl groups attached to perfluoroalkylene groups generally require temperatures greater than about 300° C. to dimerize and are subject to isomerization.

Preferably, X is independently selected from the group consisting of groups having at least one non-carbon atom between the perfluorovinyl groups and R, such as groups containing oxygen, sulfur, selenium atoms, tellurium atoms, silicon, boron, phosphorus or nitrogen between R and the perfluorovinyl group, e.g. oxygen atoms, sulfur atoms, (thio) carboxylic ester groups, phosphines, (thio) carbonyl groups, seleno, telluro, silanediyl, trisilanediyl, trisilazanyl or silylthio, boranediyl groups. Preferred groups have S, O, Si, N or P, more preferably S, O or Si between R and the perfluorovinyl group, such as carbonyl, thiocarbonyl, sulfone, sulfoxy, silanediyl, amines, (optionally inertly substituted) oxygen or sulfur atoms. Most preferably there is a single atom other than carbon; even more preferably it is oxygen or sulfur, among those groups preferably an ether or sulfide linkage, because monomers having such linking structures advantageously form perfluorocyclobutane groups at lower temperatures than are needed with such groups as perfluoroalkyl groups and are more stable than monomers where the perfluorovinyl group is attached directly to R, particularly when R is aromatic. Monomers having such linking structures are also relatively easily prepared.

When these are carbon-containing structures associated with X or G, such as in ester groups, siloxane groups and the like, those carbon containing structures suitably have any number of carbon atoms, but preferably have from about 1 to about 50, more preferably from about 1 to about 12 carbon atoms.

R is suitably any inert hydrocarbyl group (that is a group having at least one carbon atom bonded to a hydrogen atom, such as methylene, phenylene, or pyridinyl group), preferably a hydrocarbyl group which facilitates formation of perfluorocyclobutane rings and/or imparts desirable physical properties to polymers or oligomers prepared from compounds of Formula I. For the purpose of imparting desirable physical properties to polymers, R preferably contains at least one carbon atom. (Preferably, the carbon atom is in the molecular chain between X and G because compounds having at least one carbon atom between X and G tend to have desirable stability and to produce polymers having desirable physical properties.) Alternatively, the carbon atom is in a side chain; for instance, —R— can be —N(CH$_3$)—, —N(CH$_2$CH$_3$)—, —P(CH$_3$)—, —P(CH$_2$CH$_3$)— and the like. The carbon atoms(s) in R are suitably in aliphatic, cycloaliphatic, aromatic, heterocyclic groups and the like and combinations thereof. Additionally, R optionally contains groups or has substituents which are inert, that is which do not undesirably interfere with the formation of perfluorocyclobutane rings from perfluorovinyl groups. Inert substituents include ether, carbonyl, ester, tertiary amide, carbonate, sulfide, sulfoxide, sulfone, nitrile, alkyl phosphonate, tertiary amine, alkyl phosphate, alkyl silyl, chlorine, bromine, fluorine, alkyl, arylalkyl, alkylaryl, cycloalkyl, aromatic, heterocyclic, alkoxyl, aryloxy groups and the like. Carbon-containing inert substituents on R preferably contain from about 1 to about 50, more preferably from about 1 to about 12 carbon atoms because of the stability and ease of working with monomers of lower molecular weight. R, including inert substituents preferably has a molecular weight (MW) of from about 14 to about 20,000, more preferably from about 75 to about 15,000 and most preferably from about 75 to about 5,000. These ranges include monomeric and oligomeric R groups. In the case of monomers which are other than oligomeric, R preferably has from about 1 to about 50, more preferably from about 6 to about 25, carbon atoms because molecular weights above this reduce the contribution to properties made by the fluorine-containing substituents when R is alkyl or aromatic hydrocarbon. As previously discussed, the nature of R as well as the perfluorocyclobutane content of the polymers can vary broadly according to the type of products desired.

Preferably, for polymers having good plastic properties such as tensile strength and flexibility, at least one carbon atom of R is in the molecular chain between X and G and is part of an aromatic nucleus. Aromatic groups are desirable because of improved physical properties of the polymers and ease of manufacture of the monomers. For both ease of manufacture of the monomer and monomer stability, when R is aromatic, each X is preferably a group having only non-carbon atoms, more preferably one non-carbon atom, most preferably one non-carbon atom is sulfur or oxygen between R and the perfluorovinyl group. The aromatic group can be any molecular structure having aromatic character, advantageously having at least one six membered aromatic ring, suitably having any number of such six-membered rings fused together or connected by bonds or linking structures. R preferably has from about 1 to about 50 such rings, more preferably from about 1 to about 10 rings, more preferably containing from about 6 to about 25 carbon atoms, most preferably R has at least 2 to about 4 aromatic rings to impart properties such as hardness and/or stiffness to a polymer. The aromatic fragment is suitably unsubstituted or inertly substituted. Inert substituents on an aromatic R include, for instance, the inert substituents listed for R generally. Exemplary aromatic molecular fragments include, for instance, perchlorophenylene, phenylene, biphenylene, naphthylene, dichlorophenylene, nitrophenylene, p,p'(2,2-diphenylene propane) [—$C_6H_4$—$C(CH_3)_2$—$C_6H_4$]; p,p'-(2,2-diphenylene-1,1,1,3,3,3-hexafluoropropane) [—$C_6H_4$—$C(CF_3)_2$—$C_6H_4$—], preferably biphenylene; phenylene; 9,9'-diphenylfluorene, oxydiphenylene; thiodiphenylene: 2,2-diphenylene propane; 2,2'-diphenylene, 1,1,1,3,3,3-hexafluoropropane; 1,1-diphenylene-1-phenyl ethane: naphthalene; and anthracene. Molecular weights of aromatic ring containing polymers are preferably at least about 10,000. Such aromatic groups are preferably present because they generally impart high temperature glass transition properties (Tg) and good mechanical strength (e.g. as measured by differential scanning calorimetry (DSC) and tensile/flexural tests) to the polymer.

Most preferably, at least one aromatic carbon atom of R is bonded directly to X because perfluorovinyl groups bonded to X, said X being bonded to aromatic groups are generally more reactive in forming perfluorocyclobutane rings.

Compounds having a perfluorovinyl group and a functional group are advantageously formed by chemically reacting a compound having a perfluorovinyl group with a compound having a suitable functional group or a molecular structure suitable for conversion to a functional group (e.g. by techniques disclosed in such references as Antonucci, High Polymers, Vol. XXV, "Fluoropolymers," Chapter 2, "The Synthesis and Polymerization of Fluorostyrenes and Fluorinated Vinyl Phenyl Ethers," pp. 33–82 (1972): or, preferably by forming a compound having a functional group or a molecular structure suitable for conversion to a functional group and a molecular structure suitable for conversion to a perfluorovinyl group, then converting that structure to the perfluorovinyl group. In either case, a molecular structure suitable for conversion to a functional group is then converted to the functional group.

Preferably, the process comprises the steps of:

(a) preparing a 2-halotetrafluoro compound of the Formula III:

(Q—$CF_2$—$CF_2$-X-)$_m$R-(-G")$_n$ wherein X, R, m and n are as previously defined; Q is bromine, chlorine or iodine; preferably bromine or iodine, most preferably bromine; and G" is a functional group G, as previously defined, or a functional group suitable for conversion into G; and (b) chemically modifying group G" to produce functional group G (c) dehalogenating the 2-halotetrafluoro compound to form the corresponding trifluorovinyl compound.

Step (b) optionally precedes or follows step (c), or steps (b) and (c) are simultaneous, generally depending on the relative ease of the reactions required and the relative sensitivity of the 2-halotetrafluoro group or the trifluorovinyl group to the chemical reactions required for step (b).

Generally, the trifluorovinyl group is sensitive to materials more nucleophilic than amines such as metal hydroxides (e.g. potassium and sodium hydroxide), metal alkoxides, metal sulfides, metal alkylthiolates, metalamides, metal alkylamines and organometallics. Reactions involving such materials are avoided after formation of the trifluorovinyl group.

Compounds of Formula III are suitably prepared by any method within the skill in the art such as by processes taught by Rico et al. in U.S. Pat. No. 4,377,711: by Carl et al. in U.S. Pat. No. 4,423,249 which patents are incorporated by reference herein; by Antonucci in High Polymers Vol. XXV, ed. Walls, Wiley Interscience (1972) and references therein; by Xingya in Tetrahedron Letters, 1984, 25 (43), 4937–4940 and references therein.

Preferably they are prepared by a process including the steps of:

(a) forming a salt having an anion represented by Formula IV:

(-X)$_m$-R-(G")$_n$ (b) reacting the salt with a 1,2-dihalo-1,1,2,2-tetrafluoroethane wherein the halo (halogen) groups are as defined for Q in Formula III, but at least one of the halo groups is bromine or iodine.

Salts having anions of Formula IV are suitably formed by any method which associates a metal cation with such an anion such as replacing hydrogen atoms of compounds such as those of Formula V:

(HX)$_m$—R—(G")$_n$ with metal cations. Suitable methods include reaction with bases such as sodium hydroxide or potassium hydroxide when the compound has an acidity sufficiently high to react with a hydroxides, such as when R is aromatic carbocyclic or aromatic heterocyclic. Compounds of lower acidity are reacted, for instance, with metals such as sodium or their hydrides. Among hydroxides, potassium hydroxide is generally preferred because potassium salts of alkoxides or aryloxides are more reactive than are lithium or sodium salts, for instance, sufficient hydroxide or metal to form the salt is used, preferably at least about 1.0 equivalents of hydroxide of metal per equivalent of compound of Formula V. Suitable temperatures and pressures are determined without undue experimentation and are conveniently atmospheric pressure and a temperature maintained below about 140° C. to avoid ring halogenation when there is an aromatic ring in the compound. Temperatures are preferably from about −10° C. to about 125° C. for an aromatic compound (R is aromatic) and of from about −25° C. to about 25° C. for an alkyl compound Suitably, both the compound of Formula V and the hydroxide are slurried or dissolved in an easily removable medium such as methanol before reaction for convenience in mixing the reactants. Alternatively, and preferably, the hydroxide is mixed directly into a solution of the compound of Formula V in a solvent such as methanol, a glyme, water or mixtures thereof.

Alternatively, salts may be formed by reaction of compounds of Formula V with metals or their hydrides such as Group I metals including sodium and potassium or any metal or its hydride which reacts to form salts with compounds of Formula V at temperatures of from about $-25°$ C. to about 150° C. These reactions are particularly useful when $(H-X)_m-R-(G'')_n$ is unreactive toward metal hydroxides. Use of metals and their hydrides is within the skill in the art and is found, for instance in Fieser and Fieser, Reagents for Organic Synthesis, Wiley-Interscience, New York (1967).

Although it is generally preferable for convenience, to maintain reactants in a slurry or solution for subsequent reaction, any liquid medium, e.g. methanol or glyme is suitably, alternatively, removed before the next reaction step. Removal of protic media is necessary. Removal is within the skill in the art. Methanol, for instance is conveniently removed by rotary evaporation followed by heating to about 100°–140° C. under vacuum until the salt is dry. Other media are conveniently removed, for instance, by filtration, spray-drying particularly of water solutions, or freeze-drying.

The salt is then reacted with a 1,2-dihalo-1,1,2,2-tetrafluoroethane which is commercially available.

The dihalotetrafluoroethane has a structure represented by Formula VI

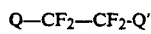

Q—CF$_2$—CF$_2$-Q' wherein Q and Q' represent halogens other than fluorine. Q and Q' are preferably selected such that the tetrafluoroethane reacts readily with the anion (preferably of Formula IV), leaving one halogen (Q or Q'), and that halogen is later readily eliminated to form a perfluorovinyl group. Q and Q' are, therefore, preferably selected from Cl, Br, and I and at least one of Q and Q' is Br or I; more preferably Q and Q' are independently Br or I; most preferably Q and Q' are Br. 1,2-dibromo-1,1,2,2-tetrafluoroethane is preferred because it is liquid at room temperature, stable, and readily available.

The 1,2-dihalotetrafluoroethane is preferably reacted with the salt in a liquid reaction medium which is, for instance, suitably a solution or slurry of the salt in an aprotic solvent such as an ether, (e.g. diethyl ether), dioxane, dimethyl sulfoxide (DMSO), glyme, diglyme, tetraglyme, tetrahydrofuran, dimethyl formamide (DMF), or acetonitrile. The glymes, DMSO and DMF are preferred, with DMSO most preferred but DMF most preferred at low temperatures below which DMSO begins to freeze. When the reaction medium is a slurry it is preferably stirred sufficiently to maintain the slurry and contact between the dihalotetrafluoroethane and the salt. Sufficient solvent to homogeneously disperse both the dihalotetrafluoroethane and the salt is used, preferably from about 1 to about 99, more preferably from about 25 to about 75 weight percent solvent relative to weight of salt, for convenience. Sufficient salt is reacted with the dihalotetrafluoroethane to form a predetermined degree of substitution: preferably from about 0.1 to about 10.0 equivalents of salt per equivalent of dihalotetrafluoroethane is supplied, more preferably from about 0.75 to about 1.1 equivalent of salt. The dihalotetrafluoroethane is preferably added as a liquid at room temperature or with cooling and/or pressure if necessary to maintain the liquid phase.

The reaction temperature is preferably maintained above $-30°$ C. to achieve reaction at a convenient rate and below 125° C. to avoid by-products. More preferably the temperature is maintained between about $-10°$ C. and about 125° C., most preferably between about 0° and about 125° when R is aromatic and X is —O—, —S—, —SO$_2$— or —SO—; most preferably between about $-10°$ C. and about 25° C. when R is alkyl. These temperatures are preferably used at atmospheric pressure which is preferable for convenience. Alternatively sub- or super-atmospheric pressure is used and temperature adjustments within the skill in the art are made. The temperature of the reaction is also dependent on the nature of a substituent group. In general, electron donating substituents enhance the reaction, and cooling is necessary to keep the reaction temperature down. Electron donating substituents also activate the aromatic ring toward halogenation which can be a significant side reaction at elevated temperatures. The reactions are preferably run at the lowest temperature possible to prevent ring halogenation. Electron withdrawing substituents, however, retard the reaction and deactivate the ring toward halogenation. Reactions involving deactivated phenols are preferably heated to obtain a convenient reaction rate. The deactivated phenols can be heated much hotter than the activated phenols, because the deactivating groups also retard ring halogenation. In all cases the reaction is advantageously kept substantially free of protic materials, which are preferably at concentrations of less than about 0.1 weight percent, most preferably in no detectable concentrations. Protic materials can cause production of an undesirable side product (i.e. —OCF$_2$CF$_2$H instead of —OCF$_2$CF$_2$Br). Protic materials include water, alcohols, phenols and the like.

When aromatic ethers are formed, the ease of the reaction of a phenol salt and 1,2-dihalotetrafluoroethylene is correlatable to the pKa (acidity) of the parent phenol. The presence of an electron-withdrawing substituent retards the reaction, and decreases the pKa of a phenol; increasing temperatures are required to obtain ether formation. A comparison of the pKa's of substituted phenols and reaction temperature for ether formation is shown in Table 4.

TABLE 4

| Aromatic substituent | pKa (para) | Rxn Temp. °C. | pKa (meta) | Rxn Temp. °C. |
|---|---|---|---|---|
| —CH$_3$ | 10.26 | 0–20 | 10.00 | — |
| —OCH$_3$ | 10.2 | 0–20 | 9.65 | — |
| —OC$_2$H$_3$ | 10.0 | 10–20 | 10.07 | 0–20 |
| —H | 9.99 | 20–25 | 9.99 | 20–25 |
| —F | 9.89 | — | 9.29 | — |
| —Cl | 9.43 | — | 9.1 | — |
| —Br | 9.34 | 65 | 9.03 | — |
| —CO2— | 9.23 | 65 | 9.85 | — |
| —CO2CH3 | 9.2 | 65 | 9.8 | — |
| —C(O)CH3 | 8.05 | 70–85 | 9.19 | — |
| —CN | 7.95 | — | — | — |
| —CHO | 7.62 | 75–85 | 9.0 | — |
| —NO2 | 7.15 | >90 | 8.36 | — |

Some substituent groups, for example, ketones and aldehydes, are capable of reacting with a hypobromite intermediate. These reactive substituent groups are best protected (e.g. as acetals) prior to reaction. It is observed that meta-substituted phenoxides, in most cases, react at lower temperatures than corresponding para-substituted phenoxides.

Reaction of a 1,2-dihalotetrafluoroethane and the salt forms a 2-halotetrafluoroethyl compound. The 2- halotetrafluoroethyl compound is either separated from the liquid media or slurry or is further reacted in the medium. Removal is by means within the skill in the art, such as by pouring the slurry into an equal volume of water and removing the product in a lower, oily layer which is then purified by vacuum distillation. If a liquid medium such as tetraglyme which does not completely dissolve in water is used, the product is conveniently distilled therefrom under vacuum. Otherwise, the product in a solvent such as a glyme (including multiple glymes such as diglyme and tetraglyme) conveniently filtered from the precipitated salts, and isolated by distillation or used without purification in the dehalogenation reaction. It is preferable to remove the solvent if a different solvent is preferred for the dehalogenation reaction, also, any unreacted dihalotetrafluoroethane is preferably removed prior to dehalogenation to avoid production of by-products.

The non-fluorine halogen atom and a fluorine atom are then eliminated from the product 2-halotetrafluoroethyl compound to form the perfluorovinyl compound. The elimination is suitably conducted by any effective means. Preferably a metallic reagent such as magnesium or zinc, (more preferably zinc) is reacted with the 2-halotetrafluoroethyl compound, preferably in a liquid medium such as the ones suitable for formation of the salt. Alternatively, some reactants are sufficiently liquid for convenient reaction in the neat form. More preferably, the 2-halotetrafluoroethyl compound is added to a hot (about 75°-140° C.) preferably about 110°-115° C. slurry of (preferably granular) zinc most preferably in a dry glyme, or other liquid medium which is aprotic. The reaction is exothermic and the temperature is regulated by the speed of the addition of reactants. Most preferably, the halotetrafluoroethyl compound is mixed with the metallic agent in a dry glyme and refluxed at about 85°-90° C. with stirring until the perfluorovinyl compound is formed, generally several hours, conveniently overnight. Better yields are generally observed in glymes. Zinc is preferred not only because of its effectiveness but also because few substituent groups (other than possibly nitro groups) on aromatic portions of the molecule react with zinc. Granular zinc is convenient to work with, but size has little effect on the reaction except that powdered zinc increases reaction rate to vigorous level. The zinc is preferably cleaned by washing with dilute acid (e.g. hydrochloric acid), rinsing with water and drying under vacuum. This method enhances initiation of the elimination reaction and accelerates the rate of that reaction.

Efficient stirring is important to avoid occluding the active metallic reagent in a heavy precipitate of metallic salts. Dehalogenation is exothermic, and if carried out at 110°-115° C., the addition rate of a dihalotetrafluoroethyl ether to the reaction mixture is preferably controlled to avoid overheating. It is preferable to adjust the rate of addition so that the reaction maintains itself at about 110°-115° C. without external heating.

After completion of the reaction, any precipitated materials, e.g. metal salts are removed, by methods within the skill in the art, conveniently by centrifugation because the precipitates are often very fine. If diglyme or tetraglyme or higher boiling solvent is used, the product is preferably fractionally distilled from the mixture. If glyme or a lower boiling solvent is used, the solvent is conveniently removed by rotary evaporation and the product is preferably purified by distillation.

In a preferred embodiment of the invention, compounds having a structure corresponding to Formula I, are reacted with other materials suitable for incorporation into polymers The materials include reactive oligomers, difunctional compounds, polyfunctional compounds and the like. Polyfunctional compounds suitably have any number of reactive functional groups, preferably from about 2 to about 10, more preferably from about 2 to about 4 functional groups. Such reactions are referred to herein as "capping", and the compounds of Formula I so used as "capping agents". Preferably, the compounds of Formula I are reacted with oligomers (polymers having from about two to about 100 repeating units and, preferably, a molecular weight of from about 300 to about 30,000); or alternatively with di- and poly-functional compounds (such that at least one group suitable for reaction to form a polymer remains). These compounds, oligomers or relatively low molecular weight polymers are then preferably thermally reacted such that the perfluorovinyl groups form perfluorocyclobutane groups and the molecular weight of a resulting material is increased. Use of such compounds is given in further detail in copending U.S. applications Ser. No. 364,667 filed Jun. 9, 1989 now U.S. Pat. No. 5,037,917, and Ser. No. 364,665 filed Jun. 9, 1989, now U.S. Pat. No. 5,023,380, simultaneously herewith, which are incorporated herein in their entirety.

Compounds of the invention are reacted with relatively low molecular weight (e.g. from about 300 to 30,000, preferably from about 1000 to about 20,000, more preferably from about 1000 to about 5000) oligomers or polymers to form perfluorovinyl terminated polymers or oligomers. The polymers or oligomers are preferably those that have a low viscosity relative to their higher molecular weight counterparts, suitably low molecular weight polymers containing perfluorocyclobutane rings, addition polymers (including addition polymers of perfluorovinyl compounds) or condensation polymers such as polyethers, poly(carboxylic acid derivatives) including polyesters, polyurethanes, epoxy resins, polysulfones, polycarbonates and polyamide-polyimides: preferably polycarbonates, polyesters, polyamides, polyimides and the like, more preferably polyimides, liquid crystal polymers, especially polyesters, aromatic polyesters, aromatic polyamides, aromatic polycarbonates and the like which are frequently intractable or have high melting points and poor melt flow characteristics at temperatures commonly used in shaping or molding polymers, when advanced to high molecular weights such as molecular weights greater than about 10,000. To be useful in reacting with compounds of Formula I having functional group G, the oligomers or polymers must have a group reactive with G. Examples of suitable terminal groups of the oligomers or polymers include carboxylic acid groups and their derivatives such as salts, acid halides, or esters: amines, either primary or secondary; hydroxyl; chloroformate or any number of other nucleophilic or electrophilic groups. When one of either the compound of Formula I or the polymer or oligomer has a given reactive group, the other has a functional group of opposite reactivity, i.e. nucleophilic with electrophilic. Preferably the perfluorovinyl group is incorporated as a perfluorovinyl ether, more preferably a perfluorovinyl aromatic ether, most preferably as the perfluorovinyl ether of an aromatic ester, as for example $CF_2=CF-O-Ar-CO-O$-oligomer where Ar is an aromatic group. An example of the latter method of preparing the monomer and subsequently the polymer of the present embodiment of the invention is the reaction of polycarbonate oligomer or other oligomer having terminal phenolic groups with 4-trifluorovinyloxybenzoyl chloride. The resulting oligomeric compound is terminated with trifluorovinyl groups connected to the oligomer via ester groups formed in the reaction of the phenolic end groups with the acid chloride reactive site of the trifluorovinyl compound. The reaction is conveniently conducted by methods of forming esters from phenolics and acid chlorides. Oligomers, thus capped, are then thermally polymerized to a higher molecular weight polymer wherein the oligomer fragments are linearly linked by perfluorocyclobutane rings. Polymers, thus formed, retain substantial property similarity to high molecular weight resins of the oligomer structure. The 4-trifluorovinyloxybenzoyl chloride referred to above and related compounds are prepared from phenolic substituted aromatic esters by techniques taught in U.S. Pat. No. 4,423,249, which is incorporated herein by reference, followed by hydrolysis to the acid and then conversion to the corresponding acid chloride.

Alternatively, the compounds of Formula I are similarly reacted with di- or poly-functional compounds such as diphenols, e.g. 4,4'-biphenyldiphenol: dianilines; diacyl chlorides, e.g. terephthaloyl chloride: hydroxy carboxylic acids, e.g. hydroxy benzoic acid and the like.

Reaction products of such reactions are generally useful in further reactions, including polymerization. For instance, compounds having two or more perfluorovinyl groups are useful for polymerization according to the teaching of U.S. application Ser. No. 364,667 filed Jun. 9, 1989 now U.S. Pat. No. 5,037,917 which is incorporated by reference herein in its entirety. Alternatively, products of the reaction of Formula I with polyfunctional compounds having more than one type of functional group, less than all of which are reactive with the compound of Formula I have perfluorovinyl groups and remaining functional groups. The functional groups are useful for reacting e.g. with oligomers polymers or compounds to form compounds suitable for coupling or polymerization to form higher molecular weight compounds by thermally forming perfluorocyclobutane rings. Alternatively, perfluorocyclobutane rings are formed before the functional groups are reacted.

Alternatively, compounds having a perfluorocyclobutane group and at least two functional groups are prepared by thermally dimerizing compounds of the invention and converting the suitable groups to the functional groups as appropriate.

Thus, compounds of Formula II are formed by a process comprising steps a through c explained above and step (d) after step (c), thermally dimerizing the trifluorovinyl compound to form a compound having a perfluorocyclobutane group.

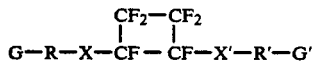

wherein X, R and G are as previously defined and X' is independently defined as is X, R' is independently defined as is R and G' is independently defined as is G. More detail regarding these novel compounds is given in U.S. application Ser. No. 364,686 filed Jun. 9, 1989 now U.S. Pat. No. 5,021,607, which is incorporated herein in its entirety.

In the process, step d follows step c, but step (b) optionally precedes or follows step (c) or (d), depending on the relative sensitivity of the groups present to subsequent reactions. Determining suitable order of reaction steps is within the state of the art without undue experimentation.

The perfluorovinyl compounds are preferably thermally dimerized by heating the compounds to a temperature and for a time sufficient to form perfluorocyclobutane rings. Temperatures suitable for forming perfluorocyclobutane rings differ with the structure of the perfluorovinyl compound. In general, temperatures above about 40° C. are suitable for formation of perfluorocyclobutane rings, preferably the temperature is above about 50° C., more preferably above about 100° C., because these temperatures result in formation of the rings at successively faster rates. Dimerizations are preferably carried out by stirring and heating the neat perfluorovinyl compounds under nitrogen to approximately 195° C. for several hours Temperatures above about 450° C. are preferably avoided because perfluorocyclobutane rings are thermally unstable at such temperatures.

Preferably, especially when the perfluorovinyl compounds are capable of addition polymerization, like formation of polytetrafluoroethylene, conditions conducive to free radical polymerization, e.g. presence of oxygen, ozone, peroxygen compounds and other free radical generating compounds, are avoided so that the perfluorovinyl groups will dimerize into perfluorocyclobutane groups rather than addition polymerizing. Compounds known in the art for stabilization against free radical polymerization are alternatively used. Such compounds include limonene and phenolic compounds. Similarly, especially when the perfluorovinyl groups are capable of addition polymerization in the presence of anions or cations, compounds which supply such anions or cations are avoided. For instance, fluoride (e.g. from carbonyl fluorides), chloride, hydroxide, phenoxide ions and the like are preferably avoided. To avoid such compounds as carbonyl fluorides, oxidative conditions such as presence of oxygen, hypochlorite, dichromate, permanganate and the like are preferably avoided because perfluorovinyl groups are known to oxidize to form carbonyl fluorides. Perfluorovinyl ethers, thioethers, sulfones, sulfoxides and the like are relatively stable with regard to addition polymerization and oxidation; and, therefore, such precautions are generally unnecessary when these perfluorovinyl compounds are used.

Advantageously, the perfluorovinyl compounds are stirred while they are heated Perfluorovinyl compounds or admixtures thereof are preferably neat or, alternatively are in admixture with other materials such as in solution, in emulsion, in dispersions or in any other form in which perfluorovinyl compound molecules can be contacted with one another to form a dimer. Liquid admixtures are advantageous for maintaining contact between perfluorovinyl compound molecules such that dimers are formed.

Dimerizing suitably takes place at any pressure. Pressures of about one atmosphere are generally preferable for convenience when the perfluorovinyl compounds and any solvents and/or dispersing media remain liquid at the temperatures used for dimerizing. Other pressures are also suitably used, and are especially useful when the perfluorovinyl compounds have boiling points below the optimum dimerization range. Unreacted perfluorovinyl compounds along with any tetrafluoroethyl byproducts are preferably removed from the high boiling dimer by distillation at reduced pressure. The dimer is conveniently then distilled under high vacuum for further purification. Alternatively, other purification methods within the skill in the art are used.

The perfluorovinyl compounds may contain functional groups as described for G and G' in Formulas I and II such as alkoxy and alkyl when R is aromatic, halide, ester, acid, ketone, aldehyde, nitro, nitrile, alkylthio groups which do not react undesirably with the perfluorovinyl compound or interfere with formation of its dimer, the perfluorocyclobutane compound. Alternatively, the perfluorovinyl compound can have a molecular structure suitable for conversion to a functional group (G" in Formula III). Conversion after dimer formation is preferred when the functional group for condensation polymerization is reactive with a perfluorovinyl group or would undergo polymerization at reaction temperatures. Exemplary of such groups are esters which are convertable to acid chloride by saponification followed by treatment with oxalyl chloride (for perfluorovinyl group compounds) or thionyl chloride for perfluorocyclobutane compounds according to the procedures disclosed by J. Cason *Org. Syn.*, Coll. Vol. 3, 169 (1955); methoxy groups which are convertable to hydroxy groups by treatment with NaI and Me$_3$SiCl in CH$_3$CN according to the procedures disclosed by Olah in *J. Org. Chem.* 1979, 44, 1247–1251; ethyl groups on perfluorocyclobutane compounds which are convertable to ethynyl groups by procedures detailed in examples of the invention; esters which are convertable to acid chloride and subsequent conversion to isocyanates by Curtius rearrangement according to the procedures disclosed by P. Smith in Organic Reactions, Vol. 3, pp. 337–449, Wiley, NY ed. Adams (1946), to amines by Curtius reaction according to the procedures disclosed by P. Smith in Org. Reactions, vol. 3, pp. 337–449, ed. Adams, Wiley, NY (1946). Those skilled in the art are familiar with other such conversions. Examples of the invention provide additional detail with regard to useful conversions.

Details of forming and using such dimers are given in copending U.S. application Ser. No. 364,686 filed Jun. 9, 1989, now U.S. Pat. No. 5,021,607.

The following examples are offered to illustrate but not to limit the invention. In each case, percentages are by weight unless otherwise indicated. Examples (Ex.) of the invention are indicated numerically, while comparative samples (C.S.) are not examples of the invention and are indicated with letters In each case, gas chromatographic (GC) analyses are done on a Varian 3700 GC using a 30 m DB210 megabore column (commercially available from J&W Scientific) and a flame ionization detector The conditions are: injector, 150° C.; detector, 250° C.: temperature program: 50° C. for 3 min, then increase 10° C./min to 180° C. and hold; initial column pressure 20 psig (pounds per square inch guage). Proton nuclear magnetic resonance (NMR) spectra are taken on a EM-360 or T-60 (Varian) nuclear magnetic resonance spectrometer. Fluorine (19 F) NMR's are taken on a Varian EM-360 modified for 19F NMR using trifluoroacetic acid (TFA) as the external zero reference. The 19F NMR spectra of the 2-bromotetrafluoroethylethers appears as two triplets within the ranges of: (CF$_2$Br)-10.2 to -9 ppm (J approximately 7-9Hz) and (CF$_2$O) 7.8 to 9.5 ppm (J cis approximately 7-9Hz) The 19F NMR spectra of the trifluorovinyl ether appears as 3 doublets of doublets within the ranges of: (=CF, cis to F) 39 to 45 ppm, (J approximately 60 Hz, J gem approximately 100 to 107 Hz). (=CF, trans to F) 45 to 52 ppm, (J trans approximately 112 to 120 Hz, J gem approximately 100 to 107 Hz); (OCF) 55 to 60 ppm, (J trans approximately 112 to 120 Hz, J cis approximately 60 Hz). The 19F NMR spectra of the substituted perfluorocyclobutane rings appears as broad multiplets at 48 to 55 ppm. Infrared analyses are performed on a Beckman IR-33 or a FTIR (Fourier transform infrared spectrometer) to obtain spectra characteristic of the respective functional groups and characteristic of a perfluorovinyl group at 1845 cm$^{-1}$. Thermal data are obtained on a Perkin-Elmer 7 Series Thermal Analysis System according to manufacturer's directions. Gas chromatography/mass spectrometry (GC/MS) is performed on a Finnigan 1020 using a 30 m RLS 150 capillary column. Conditions are varied to give the best combinations of retention time and resolution.

EXAMPLE 1: PREPARATION OF METHYL 4-TRIFLUOROETHENYLOXYBENZOATE, DIMERIZATION AND DERIVATION TO FORM 1,2-BIS(4-CHLOROFORMYLPHENOXY)HEXAFLUOROCYCLOBUTANE

Methyl p-hydroxybenzoate is converted to its potassium salt by reaction with a stoichiometric amount of potassium hydroxide in methanol. The salt is isolated by evaporation and dried under vacuum. The dried salt is slurried in an equal weight of dry dimethyl sulfoxide. The mixture is stirred and heated to about 50° C. and a slight excess of 1,2-dibromotetrafluoroethane is added slowly. The reaction temperature is maintained at 60°–70° C. An efficient condenser is necessary to condense the dibromotetrafluoroethane. After addition is complete, the mixture is warmed for an additional hour, cooled and poured into an equal volume of water. The product (methyl 4-(2-bromotetrafluoroethoxy)benzoate) separates as a brown oil which is distilled under vacuum (85°–90° C., 0.3 torr) to yield a colorless oil (85-95% yield).

The bromotetrafluoroethylether is dehalogenated by combining it with a stoichiometric amount of granular zinc in glyme and refluxing overnight. After removal of the glyme by evaporation, the product, methyl 4-trifluoroethenyloxybenzoate, is distilled under vacuum (85°–90° C./8–10mmHg, 85-100% yield).

The methyl 4-trifluoroethenyloxybenzoate is cyclodimerized by heating at 195° C. for several hours. The dimerized product is isolated by distillation (135°–150° C./0.025mmHg, 97% yield, with the remainder being unreacted vinyl compound). The overall yield from methyl p-hydroxybenzoate is 80%.

The dimer is saponified to the diacid with 2.1 molar equivalents of sodium hydroxide in methanol Upon acidification with concentrated hydrochloric acid the diacid precipitates and is filtered from the liquid as an insoluble white powder with a melting point above 300° C. Yields are quantitative. The diacid is converted to the diacid chloride by slurrying it in approximately a 6 molar equivalent of thionyl chloride and warming the mixture to 50°–75° C. The product diacid chloride is soluble in dichloromethane and is purified by dissolving the crude reaction product in dichloromethane and filtering the diacid chloride solution from unreacted diacid (which is insoluble). The product is identified by 19FNMR, HNMR and infrared (IR) spectra. IR 1790, 1755 cm$^{-1}$ (C=O), no CO2H absorption.

EXAMPLE 2: PREPARATION OF 4-TRIFLUOROETHENYLOXYANISOLE, DIMERIZATION AND DERIVATION TO FORM 1,2-BIS(4-HYDROXYPHENOXY)HEXA-FLUOROCYCLOBUTAN

4-Methoxyphenol is converted to its potassium salt by reaction with a stoichiometric amount of potassium hydroxide in methanol. The salt is isolated by evaporation and dried under vacuum. The dried salt is slurried in an equal weight of dry dimethyl sulfoxide. The mixture is stirred and cooled in an ice bath as a slight excess of 1,2-dibromotetrafluoroethane is added slowly to maintain the reaction temperature at <30° C. After addition is complete, the mixture is warmed to 50° C. for an additional hour, cooled and poured into an equal volume of cold water. The product, 4-(2bromotetrafluoroethoxy)anisole, separates as a brown oil which is distilled under vacuum (85°-100° C., 3.5 mmHg) to yield a colorless oil (88.2% yield).

The bromotetrafluoroethylether is dehalogenated by combining it with a stoichiometric amount of granular zinc in glyme and refluxing overnight. After removal of the glyme by evaporation, the product, 4-trifluoroethenyloxyanisole, is distilled under vacuum (70° C./2.75 mmHg, 73% yield). This vinyl ether is cyclodimerized by heating at 195° C. for six hours. The dimerized product, 1,2-bis(4-methoxyphenoxy)hexafluorocyclobutane, is isolated by distillation (120°-130° C./0.05 mmHg, 91.3% yield).

The bis(methyl ether) is converted to the bis(trimethylsilyl)ether by treatment with four equivalents of trimethylchlorosilane and sodium iodide in refluxing acetonitrile for 48 hours. The bis(trimethylsilyl)ether is then hydrolyzed to the bisphenol by the addition of water, and the bisphenol is extracted with ether. The ether extracts are washed with sodium thiosulfate and concentrated to yield 1,2-bis(4-hydroxyphenoxy) hexafluorocyclobutane as yellowish crystals. The crystals are slurried in methylene chloride, chilled, and filtered to yield white crystals of 1,2-bis(4-hydroxyphenoxy)-hexafluorocyclobutane (73% conversion, 94% yield, with the remainder of the material being 1-(4-hydroxyphenoxy)-2-(4-methoxyphenoxy)hexafluorocyclobutane Identity of the product is verified using 19F NMR, 1H NMR, and IR spectra. Melting point of the bisphenol is 137°-152° C.

EXAMPLE 3: PREPARATION OF METHYL 4-(2-BROMOTETRAFLUOROETHOXY)BENZOATE AND ITS CONVERSION TO THE CORRESPONDING BENZOIC ACID AND 4-TRIFLUOROETHENYLOXYBENZOIC ACID, AND THE BENZOYL CHLORIDE THEREOF

Methyl 4-hydroxybenzoate (304.3 g, 2 mol) is dissolved in 800 mL of methanol and is converted to the potassium salt by the slow addition of potassium hydroxide (132.02 g, 2 mol, 85% purity). The resulting mixture is stirred and cooled as necessary to maintain the temperature below 50° C. The solvent is then removed by rotary evaporation and the crystalline salt is dried under vacuum overnight at 140° C.

The dried salt is allowed to cool and transferred to an oven dried 2 L flask under nitrogen. The flask is fitted with a mechanical stirrer, thermometer, heating mantle, condenser and pressure-equalizing addition funnel. Dry dimethylsulfoxide (DMSO) (550 g) is added and the mixture is stirred and warmed to 60° C. as 1,2-dibromotetrafluoroethane (537 g, 2.06 mol) is added slowly. (No appreciable reaction is observed at lower temperatures.) Reaction temperature is maintained at 65°-70° C. for two hours after addition is complete The mixture is then heated to 90° C. and allowed to cool overnight Product is isolated by extracting the mixture with 500 mL of water to remove salts and DMSO. The product separates as an orange oil which is washed with water to remove residual DMSO (The upper aqueous layer is extracted with methylene chloride and the methylene chloride solution is evaporated to yield about 40 g of product which is added to the rest of the product prior to the water washes ) The product (623 g) is distilled at 85° C./0.3 mmHg to yield 561 g of colorless oil, 85% yield. The product, methyl 4-(2-bromotetrafluoroethoxy)benzoate, is identified by 19F NMR, 1H NMR, and IR spectra.

To form the benzoic acid, methyl 4-(2-bromotetrafluoroethoxy)benzoate (33.11 g, 0.1 mol) is weighed into a 250 mL round-bottomed flask along with potassium hydroxide (85%, 8.77 g, 0.13 mol), water (5 mL) and methanol (100 mL). The mixture is stirred overnight and then acidified by the addition of 16 mL of concentrated hydrochloric acid. Product, 4-(2-bromotetrafluoroethoxy)benzoic acid, precipitates as white flocculent crystals. The methanol is removed by rotary evaporation and the product is dissolved in methylene chloride and washed with water. The methylene chloride solution is dried over magnesium sulfate, filtered and concentrated to yield 28.66 g of white crystals (yield 90.4%, m.p.170°-173° C.). The product is identified by 19F NMR, 1H NMR, and IR spectra.

To form a salt suitable for formation of the perfluorovinyl ether, another sample of methyl 4-(2-bromo-tetrafluoroethoxy) benzoate (66.25 g, 0.2 mol) is weighed into a 4-necked 500 mL round-bottomed flask fitted with a condenser, thermometer, mechanical stirrer, and heating mantle. Methanol (300mL) and sodium hydroxide (8.05 g, 0.2 mol) are added to form a mixture which is stirred and heated to reflux for three hours. A sodium carboxylate forms and begins to precipitate early in the reaction and is gelled into an almost solid mass after 1.5 hours. The mass is allowed to settle overnight and the solvent is then removed by rotary evaporation.

The sodium carboxylate is dissolved in warm water. A warm solution of zinc acetate (26.35 g, 0.12 mol) in 40 mL of water is added to precipitate the carboxylate as the zinc salt. The salt slurry is then cooled, and the zinc salt is filtered from the solution and dried under vacuum to yield 65.6 g (94% yield).

The dried zinc salt is transferred to a dry 4-necked 500 mL round-bottomed flask containing zinc metal (10 mesh, 13.0 g, 0.198 mol). Dry glyme (160 mL) is added by a canula and the flask is fitted with a condenser, mechanical stirrer, and thermometer The mixture is stirred and heated to reflux under nitrogen overnight. The mixture is acidified by the addition of 8 mL of concentrated hydrochloric acid (HCl), concentrated by rotary evaporation, and then partitioned between methylene chloride and water. The methylene chloride solution of the acid is dried over magnesium sulfate, filtered and concentrated to yield 40.02 g of 4-trifluoroethenyloxybenzoic acid as white crystals (97.6% yield, m.p. 139°-140° C.). The product 4-trifluoroethenyloxybenzoic acid is identified by 19F NMR, 1H NMR, and IR spectra.

To form the 4-trifluoroethyloxybenzoyl chloride, 4-trifluoroethenyloxybenzoic acid (79.4 g, 0.36 mol) is transferred to a 1 L round-bottomed flask. Dry methylene chloride (250 mL) is added, and the resulting mixture is stirred under nitrogen as oxalyl chloride (62.5 g, 0.49 mol) is added. The mixture is stirred overnight and then concentrated by rotary evaporation. The brown liquid is distilled at 60°–65° C./0.2 mmHg to yield 82.94 g of colorless liquid (97.4% yield). The product is identifed by 19F NMR, 1H NMR, and IR spectra.

EXAMPLE 4: REACTION OF POLYCARBONATE OLIGOMER WITH TRIFLUOROETHENYLOXYBENZOYL CHLORIDE AND CHAIN EXTENSION OF POLYCARBONATE OLIGOMERS BY CYCLODIMERIZATION OF TRIFLUOROVINYL GROUPS

Low molecular weight polycarbonate oligomer (2000 MW) terminated with bisphenol A groups (7.5 g, about $7.8 \times 10^{-3}$ mol of phenolic OH) is weighed into a 100 mL flask with trifluoroethenyloxybenzoyl chloride 30 (1.84 g, $7.8 \times 10^{-3}$ mol) as prepared in Example 3. Dichloromethane (30 mL) is added to dissolve the oligomer, and the mixture is stirred as triethylamine (0.81 g, $8 \times 10^{-3}$ mol) is added via syringe. A fine white precipitate forms in the mixture almost immediately. Dichloromethane is added to dissolve the precipitate. The resulting solution is extracted with water to remove triethylamine hydrochloride. The dichloromethane solution is dried over 4A molecular sieves, and concentrated to yield 9.06 g (100g) of oligomer capped with trifluoroethenyloxybenzoyl groups. Structure is verified by 19 F NMR (trifluorovinyl ether pattern), H-NMR (2 protons of the aromatic benzoate are shifted downfield to 8–8.3 ppm from the aromatic polycarbonate protons), and FT-IR (C=O stretch at 1739 cm$^{-1}$, distinct from the C=O stretch of polycarbonate at 1774 cm$^{-1}$).

A sample of the capped oligomer is heated to 300° C (under differential scanning calorimetry (DSC) analysis) to effect chain extension. The sample is cooled and reheated to determine the Tg, which is observed at 140.4° C. (representative of high molecular weight polycarbonate). For comparison a sample of the uncapped oligomer heated to 300° C., cooled, and reheated, exhibits a Tg of only 106.8° C. The increase of 33.6° C. in the Tg is attributed to the production of high molecular weight by linear chain extension through cyclodimerization of the trifluorovinyl groups to form perfluorocyclobutane groups.

EXAMPLES 5–14: PREPARATION AND DIMERIZATION OF SUBSTITUTED PHENYPERFLUOROVINYLETHERS

For each of Examples 5–14 the following procedure is followed with the details of solvent and reaction temperatures noted in Tables I-III. A phenol starting material having the substituent indicated in Table 1 is dissolved or slurried in methanol to form an admixture. A methanolic solution of one equivalent of potassium hydroxide is added to the stirring admixture. The admixture is cooled to maintain a temperature below 40° C. Stirring and cooling is maintained for about 15 minutes after addition is complete.

The methanol is then removed by rotary evaporation and a resulting wet salt is transferred to a suitable container and dried under vacuum at 100°–140° C. to produce a dry salt. The dry salt is transferred to a dry flask and an equal volume of dry solvent as indicated in Table 1 is added to form a slurry. The flask is fitted with a mechanical stirrer, thermometer, efficient condenser, and pressure-equalizing addition funnel.

The salt slurry is stirred and heated or cooled as indicated in Table 1 as a slight excess (1.1 equivalents) of 1,2-dibromotetrafluoroethane is added slowly. Reaction temperature is dependent on the nature of the substituent group (see Table 1). The reaction temperature is maintained for about 2 hours after addition is complete or until analysis indicates that the phenoxide is consumed and a 2-bromotetrafluoroethyl ether is formed.

The 2-bromotetrafluoroethyl ether is isolated by pouring into an equal volume of water. When the solvent is DMSO, the ether separates as a lower layer of oil and is purified by vacuum distillation. (When the solvent is tetraglyme the product is distilled from the reaction mixture under vacuum.)

TABLE 1

| EX. | Aromatic Substituent | Temp. of Reaction °C. | Heat/Cool | Solvent | Yield % of Theoretical | Product b.p. °C./mm Hg or m.p.* |
|---|---|---|---|---|---|---|
| 5 | —CH$_2$CH$_3$(p) | 25–60 | cool then heat | tetraglyme | 85 | 87/10 |
| 6 | —CH$_2$CH$_3$(m) | 25–90 | cool then heat | tetraglyme | 85 | 76–80/5 |
| 7 | —CH$_3$(p) | 30–70 | cool then heat | tetraglyme | 38 | 85/20 |
| 8 | —C(O)—CH$_3$(p) | 75 | cool then heat | tetraglyme | 27 | 100–115/1 |
| 9 | —H | 20–65 | cool then heat | tetraglyme | 64 | 70–75/20 |
| 10 | —C(O)—OCH$_3$(p) | 65 | heat | DMSO | 85–95 | 85–95/1 |
| 11 | —C(O)—OH(p) | 65 | heat saponification | DMSO | 72  85–100 from ester | 170–173 m.p. |
| 12 | —C(O)—H(p) | 75 | heat | DMSO | 60 | 60–70/1.5 |

TABLE 1-continued

| EX. | Aromatic Substituent | Temp. of Reaction °C. | Heat/Cool | Solvent | Yield % of Theoretical | Product b.p. °C./mm Hg or m.p.* |
|---|---|---|---|---|---|---|
| 13 | —BR(p) | 65 | heat | DMSO | 94 | 65/0.15 |
| 14 | —OCH$_3$(p) | 30 | cool | DMSO | 88 | 85–100/3.5 |

*Product boiling points (b.p.) are uncorrected as determined using a Kugelrohr bulb to bulb distillation apparatus and measuring container (oven) temperature. m.p. is melting point in °C.

A perfluorovinyl ether is synthesized by adding the 2-bromotetrafluoroethyl ether into a hot slurry of granular zinc in a dry glyme. When diglyme or tetraglyme is used (as indicated in Table 2) the glymes are about 105°–115° C. when the ether is added. When glyme is used, the bromotetrafluoroethyl ether is combined with granular zinc in dry glyme and refluxed at 85°–90° C. with stirring overnight. The reaction is exothermic and the temperature is regulated by the speed of the addition. For very large reactions the bromotetrafluoroethyl ether is added in portions. This method eliminates the exotherm problem and simplifies product isolation.

After completion of the reaction, the precipitated zinc salts are removed by centrifugation. If diglyme or tetraglyme is used as the solvent, the product is fractionally distilled from the mixture. If glyme is used, the solvent is removed by rotary evaporation and the product is purified by vacuum distillation.

TABLE 2

| Ex. | Phenyl Substituent | Solvent | boiling point. °C. (b.p.)/mmHg or melting point(m.p.) | Yield | Comment* |
|---|---|---|---|---|---|
| 5 | —CH$_2$CH$_3$(p) | tetraglyme | b.p. 63/15 | 94 | |
| 6 | —CH$_2$CH$_3$(m) | tetraglyme | b.p. 72/20 | 94 | |
| 7 | —CH$_3$(p) | tetraglyme | 65–70/14 | 75 | |
| 8 | —C(=O)—CH$_3$(p) | tetraglyme | 60–75/0.05 | 60 | similar bp to solvent |
| 9 | —H | tetraglyme | 96/145 | 85 | |
| 10 | —C(=O)—OCH$_3$(p) | tetraglyme | 85–90/8 | 99 | |
| 11 | —C(=O)—OH(p) | glyme | m.p. 134–140 | 99+ | form zinc carboxylic of bromofluoro ether |
| 12 | —C(=O)—H(p) | tetraglyme | purified by chromatography | 80–90 | |
| 13 | —Br(p) | glyme | 40–50/0.25 | 90+ | |
| 14 | —OCH$_3$(p) | glyme | 85–100/3.5 | 73 | |

*b.p. is boiling point

The indicated trifluorovinyl compounds are cyclodimerized by heating to 180°–195° C. for several hours, approximately 6–8 hours. Low boiling impurities and unreacted perfluorovinyl compounds are removed by vacuum distillation. The products are distilled under high vacuum and have the characteristics reported in Table 3.

TABLE 3

| Ex. | Phenyl Substituent | m.p. °C. | b.p. °C./mmHg | Yield % | Overall Yield |
|---|---|---|---|---|---|
| 5 | —CH$_2$CH$_3$(p) | | 110/0.05 | >90 | 35–40% |
| 6 | —CH$_2$CH$_3$(m) | | 120–130/0.25 | >90 | 35–40% |
| 7 | —CH$_3$(p) | | 90–120/0.05 | >90 | 20% |
| 10 | —C(=O)—OCH$_3$(p) | 67–82 | 135–150/0.025 | 97 | 80% |
| 11 | —C(=O)—OH*(p) | >300 | | 100* prep. from Ex. 10 | 80% |
| 13 | —Br(p) | | 140/0.025 | 95 | 86% |

TABLE 3-continued

| Ex. | Phenyl Substituent | m.p. °C. | b.p. °C./mmHg | Yield % | Overall Yield |
|---|---|---|---|---|---|
| 14 | —OCH₃(p) | | 120–130/0.05 | 91.3 | 59% |

*prepared by saponification of diester.

EXAMPLE 15: PREPARATION OF 4-TRIFLUOROETHENYLOXYANILINE VIA THE AMIDE 4-(2-Bromo-tetrafluoroethoxy)benzoic acid prepared as in Example 1 (26.6 g, 0.083 mol) is transferred to a 250 mL round-bottomed flask along with 150 mL of methylene chloride. Oxalyl chloride (11.64 g, 0.92 mol) is added and the mixture is stirred under nitrogen overnight to form a turbid solution which is concentrated by rotary evaporation and distilled at 80°–90° C./0.1 mmHg to yield 20.88 g of 4(2-bromotetrafluoroethoxy) benzoyl chloride as a colorless liquid, leaving 6.16 g of unreacted acid (76.8% conversion, 96.5% yield). The benzoyl chloride is added slowly with stirring to 8 mL of cold ammonium hydroxide (0.12 mol). The product amide precipitates as fine white needles which are filtered and dried under vacuum to yield 14.74 g of 4-(2-bromotetrafluoroethoxy)benzamide (75% conversion, 99% yield, m.p. 150.5°–151.5° C.), along with 4.8 g of 4-(2-bromo-tetrafluoroethoxy)benzoic acid which is recovered from the mother liquor (24.3% recovery).

The crystalline amide (10 g, 0.316 mol) is transferred to a 250 mL round-bottomed flask along with 48 mL of cold potassium hypochlorite (KOCl) solution (0.667M) containing 2 g of potassium hydroxide. The resulting mixture is stirred until most of the solids have dissolved. The mixture is then warmed in a 50°–70° C. water bath to effect the rearrangement to the amine. The mixture is extracated with methylene chloride and the extracts are dried over magnesium sulfate and concentrated by rotary evaporation. The resulting brown oil is distilled at 60°–80° C./0.05 mmHg to yield 4.85 g of 4-(2-bromo-tetrafluoroethoxy)aniline as a colorless oil (53.3% yield).

A mixture of 4-(2-bromotetrafluoroethoxy)aniline (1.44 g, 5 mmol), dry glyme (15 mL), and zinc (10 mesh, 0.4 g, 5.5 mmol) is formed and stirred with heating to reflux under nitrogen overnight. The mixture is filtered to remove insoluble zinc salts, and then concentrated to yield a cream colored solid material which is found to be the zinc complex of 4-trifluoroethenyloxyaniline.

The product amine is isolated by redissolving the complex in glyme and adding saturated aqueous sodium bicarbonate (NaHCO₃) to the solution to precipitate the zinc ion as its bicarbonate salt. The amine is extracted with methylene chloride, dried over sodium sulfate, and distilled at 45° C./0.025 mmHg to yield 0.83 g of 4-trifluoroethenyloxyaniline (88% yield) as a colorless liquid. The product is identified by 19F NMR, 1H NMR, and IR spectra.

EXAMPLE 16: PREPARATION OF 4-TRIFLUOROETHENYLOXYPHENOL

A sample of 4-trifluoroethenyloxyanisole prepared as in Example 2 is treated with two equivalents of trimethylchlorosilane and sodium iodide in refluxing acetonitrile to give 4-trifluoroethenyloxyphenol. The product is extracted with ether, washed with sodium thiosulfate solution to remove iodine, and then concentrated by rotary evaporation.

EXAMPLE 17: SYNTHESIS OF 4-TRIFLUOROETHENYLOXYPHENYL ACETATE FROM HYDROQUINONE MONOACETATE, DIMERIZATION OF THE PHENYL ACETATE AND CONVERSION TO THE CORRESPONDING PHENOL

Hydroquinone monoacetate (205.4 g, 1.35 mol), available from p-isopropylphenyl acetate by the method of Van Sickle (*Ind. Eng. Chem. Res.* 27, 440–447 (1988)), is dissolved in 800 mL of methanol and cooled to less than 10° C. with stirring. A solution of potassium hydroxide (90.9 g, 1.38 mol) in 200 mL of methanol is added slowly with cooling, keeping the reaction temperature below 20° C. The mixture is stirred for 30 minutes, then concentrated by rotary evaporation. The resulting wet salt is transferred to a crystallizing dish and dried overnight under vacuum at 120° C. The resulting dry salt is transferred to a dry 2 L, 4-necked flask fitted with a mechanical stirrer, thermometer, condenser, and pressure-equalizing addition funnel. Dry DMSO (520 g) is added to form a reaction mixture which is stirred and cooled to 10° C. The reaction mixture is stirred and maintained at 10°–20° C. as 1,2-dibromotetrafluoroethane (421 g, 1.62 mol) is added slowly. After addition is complete, the mixture is heated to 60° C. for 1 hour, cooled and poured into an equal volume of water.

Product, 4-(2-bromotetrafluoroethoxy)phenyl acetate is separated as an oily lower layer, which is washed with water to remove residual DMSO, dried over 4A molecular sieves, and distilled under vacuum (85° C./0.5 torr) to yield product 4-(2-bromotetrafluoroethoxy)phenyl acetate as a colorless oil (60–85% yield).

The product is dehalogenated by combining it with 1–2 volumes of dry glyme as solvent and 1–1.1 equivalents of zinc and refluxing with stirring overnight. The solvent is then removed by rotary evaporation, and resulting product and zinc salts are slurried in hexane or dichloromethane. The zinc salts are removed from the product by filtration, and the product 4-trifluoroethenyloxyphenyl acetate is isolated by vacuum distillation at 70°–80° C./3 torr to give the purer product as a colorless oil. The acetate is converted to 4-trifluoroethenyloxyphenol by treatment with 0.1M hydrochloric acid in methanol.

4-Trifluoroethenyloxyphenyl acetate is dimerized to 1,2-bis(4-acetoxyphenoxy)hexafluorocyclobutane by stirring and heating to 195° C. for 6–8 hours. The product is distilled under vacuum to yield 1,2-bis(4-acetoxyphenoxy)hexafluorocyclobutane as a low melting crystalline solid (m.p. 60°–80° C.).

1,2-Bis(4-acetoxyphenoxy)hexafluorocyclobutane is converted to 1,2-bis(4-hydroxyphenoxy)hexafluorocyclobutane by treatment with two molar equivalents of sodium hydroxide in methanol. The methanol is removed by rotary evaporation, and a product bisphenol is dissolved in ether, washed with water, dried over 4A molecular sieves, and concentrated to yield 1,2-bis(4-hydroxyphenoxy)hexafluorocyclobutane.

EXAMPLE 18: REACTION OF 4,4'-BIPHENOL AND TRIFLUOROVINYLOXYBENZOYL CHLORIDE

Dihydroxybiphenyl (0.7888g, 0.00423 mole) is placed in a dry 250 ml round bottom flask with a magnetic stirring bar. The flask is capped with a rubber septum. Dry methylene chloride (25 ml) and trifluorovinyloxybenzoyl chloride as prepared in Example 3 (2.000g, 0.00846 mole) are each added to the flask via syringe. The mixture is stirred as triethlyamine (0.86g, 0.0085 mole) is added dropwise. The mixture is stirred at room temperature for 2 hours, then filtered. A white precipitate is obtained and washed several times with methylene chloride to remove residual triethlamine hydrochloride. A white crystalline product is obtained and has a melting point of 225°–228° C. Qualitative solubility tests indicate that this product is nearly insoluble in methylene chloride, acetone, acetonitrile, hexane, methanol, water, and benzene, only slightly soluble in hot tetrahydrofuran, and moderately soluble in carbon tetrachloride.

Infrared analysis (using a potassium bromide KBr pellet) gives the following spectrum (reported in $cm^{-1}$): 1830, indicative of a trifluorovinyl group; 1723, indicative of a benzoate ester; 1600 and 1495, indicative of aryl carbon-carbon double bond: 1315 and 1267, indicative of carbon-fluorine bonds.

Thermal analysis (DSC) of the monomer indicates a crystalline melt beginning at 223° C., followed immediately by a slight exotherm as the monomer undergoes polymerization. A second scan of the sample shows no thermal activity up to and including 350° C.

The melted monomer exhibits possible liquid crystalline behavior during it's short lived melt phase. As viewed under a cross-polarized light microscope, the melted monomer phase (at 230° C.) exhibits birefringenoe suggestive of liquid crystalline behavior, followed by rapid polymerization to a crystalline solid. This solid does not melt, but undergoes discoloration and apparent decomposition when heated in air at temperatures above 400° C.

EXAMPLE 19: SYNTHESIS OF 1-BROMO-2,4-DI(2-TRIFLUOROETHENYLOXY)-BENZENE FROM RESORCINOL

Resorcinol (412.9 g, 3.75 mol) is dissolved in 1800 mL of DMSO and 670 mL of toluene to form a mixture in a 3-necked, 5 L flask fitted with an overhead stirrer, moisture trap and condenser, and nitrogen sparge. The mixture is stirred sparged with nitrogen as potassium hydroxide (495.1 g, 7.5 mol) is added in 5 g portions. The mixture is then heated to reflux to remove water by azeotropic distillation. After the water is removed, the mixture is cooled to 15° C. as 1,2-dibromotetrafluoroethane (2144 g, 8.25 mol) is added rapidly, and the mixture is stirred overnight. The mixture is then stirred and heated to 90° C. for three hours. The mixture is then cooled and diluted with an equal volume of water. The product separates as an oily lower layer, which is fractionally distilled under vacuum to yield 190.3 g of 1-(2-bromotetrafluoroethoxy)-3-(1,1,2,2-tetrafluoroethoxy)-benzene (3% yield), 895.5 g of 1,3-di(2-bromotetrafluoroethoxy)benzene (51% yield), and 340.8 g of 1-bromo-2,4-di(2-bromotetrafluoroethoxy)benzene (17% yield). The products are identified by 19 F NMR, H NMR, and IR spectra.

1-Bromo-2,4-di(2-bromotetrafluoroethoxy)benzene (18.06 g, 35 mmol) is added dropwise to a hot (110° C.) mixture of zinc (4.74 g, 72.5 mmol) in dry tetraglyme (20 mL). Product 1-bromo-2,4-bis(trifluoroethenyloxy)-benzene is fractionally distilled from the mixture under vacuum (95°–100° C./1 torr, 6.57 g, 59% yield). The product is identified by 19 F NMR, H NMR, and IR spectra.

What is claimed is:

1. A reaction product of a compound having a structure represented by Formula I:

wherein R represents an optionally substituted hydrocarbyl group, X represents any group which links R and a perfluorovinyl group; n is the number of G groups, m is the number of $-(XCF=CF_2)$ groups, and G represents any reactive functional group or a group convertible into a reactive functional group and a polymer wherein the reaction between the compound and the polymer takes place at G on the compound.

2. The reaction product of claim 1 wherein the polymer is an oligomer.

3. A reaction product of a compound having a structure represented by Formula I:

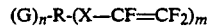

wherein R represents an optionally substituted hydrocarbyl group, X represents any group which links R and a perfluorovinyl group; n is the number of G groups, m is a number of $-(XCF=CF_2)$ groups, and G represents any reactive functional group or a group convertible into a reactive functional group and a di- or polyfunctional compound wherein the reaction between the compound of Formula I and the di- or polyfunctional compound takes place at G on the compound of Formula I.

4. The reaction product of claim 1 wherein R is an aromatic or aliphatic group which is unsubstituted or inertly substituted; and X is independently an oxygen atom, a sulfur atom, a carboxylic or thiocarboxylic ester group, a sulfone, a sulfoxide, perfluoroalkylene, perfluoroalkylene ether, alkylene, acetylene, a phosphine, a carbonyl or thio carbonyl group; seleno; telluro; nitrido; a silanediyl, trisilanediyl tetrasilanetetrayl, siloxanediyl, disiloxanediyl, trisiloxyl, trisilazanyl, or silythio group; a boranediyl or methylboranediyl group; or a combination thereof; R is an aromatic group; and wherein m and n are each independently 1 or 2.

5. The reaction product of claim 4 wherein the polymer is an oligomer.

6. The reaction product of claim 3 wherein R is an aromatic or aliphatic group which is unsubstituted or inertly substituted; and X is independently an oxygen atom, a sulfur atom, a carboxylic or thiocarboxylic ester group, a sulfone, a sulfoxide, perfluoroalkylene, perfluoroalkylene ether, alkylene, acetylene, a phosphine, a carbonyl or thio carbonyl group; seleno; telluro; nitrido; a silanediyl, trisilanediyl tetrasilanetetrayl, siloxanediyl, disiloxanediyl, trisiloxyl, trisilazanyl, or silylthio group a boranediyl or methylboranediyl group; or a combination thereof; R is an aromatic group; and wherein m and n are each independently 1 or 2.

7. A process for preparing a compound of Formula I:

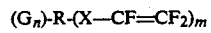

wherein R represents an optionally substituted hydrocarbyl group, X represents any group which links R and a perfluorovinyl group; n is the number of G groups, m is the number of (XCF=CF$_2$) groups; and G represents any reactive functional group or a group convertible into a reactive functional groups comprising steps of:

(a) preparing a 2-halotetrafluoro compound of the Formula III:

(Q—CF$_2$—CF$_2$-X)$_m$-R(G'')$_n$ wherein X, G, m and n are as defined for Formula I and Q is bromine, chlorine or iodine: and G'' is a functional group G, or a functional group suitable for conversion into G;

(b) chemically modifying group G'' to produce functional group G; and (c) dehalogenating the 2-halotetrafluoro compound to form the corresponding trifluorovinyl compound.

8. The process of claim 7 wherein step (a) comprises the steps of:

(1) forming a salt having an anion represented by Formula IV:

-X-R-G'

(2) reacting the salt with a 1,2-dihalo-1,1,2,2-tetrafluoroethane having as the halo groups, halogens which are bromine, iodine or chlorine or mixtures thereof, which halo groups include at least one bromine.

9. The reaction product of claim 1 wherein R is an aromatic group.

10. The reaction product of claim 9 wherein X is independently an oxygen atom, a sulfur atom, a carboxylic or thiocarboxylic ester group, a sulfone, a sulfoxide, alkylene, acetylene, a phosphine, a carbonyl or thio carbonyl group; seleno; telluro; nitrido; a silanediyl, trisilanediyl tetrasilanetetrayl, siloxanediyl, disiloxanediyl, trisiloxyl, trisilazanyl, or silylthio group; a boranediyl or methylboranediyl group; or a combination thereof.

11. The reaction product of claim 9 wherein X is bonded to an aromatic carbon atom of R.

12. The reaction product of claim 11 wherein R has from about 6 to about 25 carbon atoms.

13. The reaction product of claim 12 wherein X is oxygen, sulfur, sulfoxide or sulfone.

14. The reaction product of claim 13 wherein G is selected from hydroxyl, carboxylic or thiocarboxylic acid ester groups, carboxylic acid groups, acyl chlorides, alkyl groups when R is aromatic, isocyanates and primary or secondary amines.

15. The reaction product of claim 9 wherein R has a molecular weight of from about 14 to about 20,000.

16. The reaction product of claim 3 wherein R is an aromatic group.

17. The reaction product claim 9 wherein G is selected from hydroxyl groups (both alcoholic and phenolic), carboxylic acid groups, acyl halides, isocyanates, acyl azides, acetyl groups, primary or secondary amines, sulfide groups, sulfonic acid groups, sulfonamide groups, ketones, aldehydes, epoxy groups, primary or secondary amides; alkyl groups when R is aromatic, vinyl, allyl, acetylene groups, halo groups, nitro groups, cyano groups, anhydrides, imides, cyanate groups, trihalomethyl, alkyl or alkoxy when R is aromatic, carboxylic or thiocarboxylic acid esters.

18. The reaction product of claim 17 wherein the polymer is an oligomer.

19. The reaction product claim 16 wherein G is selected from hydroxyl groups (both alcoholic and phenolic), carboxylic acid groups, acyl halides, isocyanates, acyl azides, acetyl groups, primary or secondary amines, sulfide groups, sulfonic acid groups, sulfonamide groups, ketones, aldehydes, epoxy groups, primary or secondary amides; alkyl groups when R is aromatic, vinyl, allyl, acetylene groups, halo groups, nitro groups, cyano groups, anhydrides, imides, cyanate groups, trihalomethyl, alkyl or alkoxy when R is aromatic, carboxylic or thiocarboxylic acid esters.

20. The reaction product of claim 16 wherein X is independently an oxygen atom, a sulfur atom, a carboxylic or thiocarboxylic ester group, a sulfone, a sulfoxide, alkylene, acetylene, a phosphine, a carbonyl or thio carbonyl group; seleno; telluro; nitrido; a silanediyl, trisilanediyl tetrasilanetetrayl, siloxanediyl, disiloxanediyl, trisiloxyl, trisilazanyl, or silylthio group; a boranediyl or methylboranediyl group; or a combination thereof.

21. The reaction product of claim 16 wherein X is bonded to an aromatic carbon atom of R.

22. The reaction product of claim 21 wherein R has from about 6 to about 25 carbon atoms.

23. The reaction product of claim 22 wherein X is oxygen, sulfur, sulfoxide or sulfone.

24. The reaction product of claim 23 wherein G is selected from hydroxyl, carboxylic or thiocarboxylic acid ester groups, carboxylic acid groups, acyl chlorides, alkyl groups when R is aromatic, isocyanates and primary or secondary amines.

25. The reaction product of claim 16 wherein R has a molecular weight of from about 14 to about 20,000.

26. The reaction product of claim 1 wherein G is selected from phenolic —OH, acyl halides, isocyanates, acyl azides, acetyl groups, primary or secondary amines, sulfide groups, sulfonic acid groups, sulfonamide groups, ketones, aldehydes, primary or secondary amides; alkyl groups when R is aromatic, vinyl, allyl, acetylene groups, halo groups, nitro groups, cyano groups, anhydrides, imides, cyanate groups, trihalomethyl, alkyl or alkoxy when R is aromatic, carboxylic or thiocarboxylic acid esters.

27. The reaction product of claim 3 wherein G is selected from phenolic —OH, acyl halides, isocyanates, acyl azides, acetyl groups, primary or secondary amines, sulfide groups, sulfonic acid groups, sulfonamide groups, ketones, aldehydes, primary or secondary amides; alkyl groups when R is aromatic, vinyl, allyl, acetylene groups, halo groups, nitro groups, cyano groups, anhydrides, imides, cyanate groups, trihalomethyl, alkyl or alkoxy when R is aromatic, carboxylic or thiocarboxylic acid esters.

28. The reaction product of claim 1 wherein R represents an optionally substituted aromatic hydrocarbyl group, X represents any group which links R and a perfluorovinyl group; n is the number of G groups, m is the number of —(XCF=CF$_2$) groups, and G represents at least one phenolic hydroxyl group, acyl halide, carboxylic acid or amine group.

29. The reaction product of claim 3 wherein R represents an optionally substituted aromatic hydrocarbyl group, X represents any group which links R and a perfluorovinyl group; n is the number of G groups, m is the number of —(XCF=CF$_2$) groups, and G represents at least one phenolic hydroxyl group, acyl halide, carboxylic acid or amine group.

* * * * *